United States Patent [19]
Narayanan et al.

[11] Patent Number: 5,591,840
[45] Date of Patent: Jan. 7, 1997

[54] ANTISENSE OLIGONUCLEOTIDES DIRECTED AGAINST NUCLEIC ACIDS ENCODING NFKB TRANSCRIPTION FACTOR

[75] Inventors: Ramaswamy Narayanan, Belleville; Craig A. Rosen, Glen Ridge, both of N.J.

[73] Assignee: Hoffmann-La Roche Inc., Nutley, N.J.

[21] Appl. No.: 328,592

[22] Filed: Oct. 25, 1994

Related U.S. Application Data

[63] Continuation of Ser. No. 950,531, Sep. 23, 1992, abandoned.
[51] Int. Cl.$^6$ ............................................. C07H 21/04
[52] U.S. Cl. ......................... 536/24.5; 536/23.5; 514/44; 935/8; 935/34
[58] Field of Search .................. 536/23.1, 23.5, 536/24.5; 514/44; 935/8, 34

[56] References Cited

U.S. PATENT DOCUMENTS

| 5,138,045 | 8/1992 | Cook et al. |
| 5,225,326 | 7/1993 | Bresser et al. .............................. 435/6 |

FOREIGN PATENT DOCUMENTS

| 140308 | 3/1985 | European Pat. Off. |
| 467349 | 1/1992 | European Pat. Off. |
| WO8907614 | 8/1989 | WIPO |
| WO8908147 | 9/1989 | WIPO |
| WO9012578 | 11/1990 | WIPO |
| 92/03051 | 3/1992 | WIPO |
| 92/05284 | 4/1992 | WIPO |
| WO9220795 | 11/1992 | WIPO |

OTHER PUBLICATIONS

Sommer and Tautz, *Nucleic Acids Research*, vol. 17, No. 16, 1989, p. 6749.
Ruben et al., Molecular and Cellular Biology 12:444–454 (1992) "Functional characterization of the NF–κB p. 65 transcriptional activator and an alternatively spliced derivative".
Chiang et al., Antisense oligonucleotides inhibit intercellular adhesion molecule 1 expression by two distinct mechanisms, J. Biol. Chem. 266:18162–18171 (1991).
Calabretta, Inhibition of protooncogene expression by antisense oligodeoxynucleotides: biological and therapeutic implications, Cancer Research 51:4505–4510 (Sep. 1, 1991).
Landreth et al., Insulin–like growth factor–I regulates pro–B cell differentiation, Blood 80:1207–1212 (Sep. 1, 1992).
Denhardt, Antisense strategies come of age, The New Biologist, vol. 4, No. 5, pp. 473–481 (May 1992).
Abelda and Buck, Integrins and other cell adhesion molecules, FASEB J. 4:2868–2880 (Aug. 1990).
Lewin, Oncogenic conversion by regulatory changes in transcription factors, Cell 64:303–312 (Jan. 25, 1991).
Synthesis, vol. 1, No. 1 (Antisense Molecular Biology and "S–oligos") (Oct. 1988).
Lawlor and Narayanan, Persistent expression of the tumor suppressor gene DCC is essential for neuronal diffentiation, Cell Growth & Differentiation 3:609–616 (1992).
Narayanan et al., Antisense RNA to the putative tumor–suppressor gene DCC transforms Rat–1 fibroblasts, Oncogene 7:553–561 (1992).
Chiang et al., J. Biol. Chem. 266:18162–18171 (1991).
Calabretta, Cancer Research 51:4505–4510 (Sep. 1, 1991).
Landreth et al., Blood 80: 1207–1212 (Sep. 1, 1992).
Denhardt, The New Biologist, vol. 4, No. 5, pp. 473–481 (May 1992).
Albelda and Buck, FASEB J. 4:2868–2880 (Aug. 1990).

(List continued on next page.)

*Primary Examiner*—Bruce R. Campell
*Attorney, Agent, or Firm*—George W. Johnston; William H. Epstein; Lewis J. Kreisler

[57] ABSTRACT

The present invention is directed to oligodeoxynucleotides which are capable of hybridizing to genes which encode NF-κB. The oligodeoxyribonucleotides are antisense to NFκB genes and when hybridized prevent the production of NFκB transcription factor by the NFκB genes, and thereby provide a means for preventing cellular adhesion.

2 Claims, 8 Drawing Sheets

OTHER PUBLICATIONS

Lewin, Cell 64:303–312 (Jan. 25, 1991).
Synthesis, vol. 1, No. 1 (Antisense Molecular Biology and "S-oligos") (Oct. 1988).
Lawlor and Narayanan, Cell Growth & Differentiation 3:609–616 (1991).
Narayanan et al., Oncogene 7:553–561 (1992).
New England Biolabs 1988–89 Catalog, p. 62.
Bennet (1996) Science 271: 434.
Milligan et al (1993) J Med Chem 36:1923–1937.
Westermann et al. (1989) Biomed. Biochim. Acta 48:85–93.
Ruben, S. et al. Science 251:1490–1493 (1991).
Narayanen et al. Science 256: 367–370 (1992).
Ghosh et al. Cell 62: 1019–1029 (1990).
Kieran et al. Cell 62: 1007–1018 (1990).
Kitajima, et al. Atlation of Transplanted HTLV-1 Tax-Transformed Tumors in Mice by Antisense Inhibition of $NF-_\kappa B$, Science 258, 1792–1795 (1992).
Higgins, et al. Antisense inhibition of the p65 subunit of $NF-_\kappa B$ blocks tumorigenicity and causes tumor regression, Proc. Natl. Acad. Sci, 90 9901–9905, (1993).
Narayanan, et al, Evidence For Differential Functions of the P50 and P65 Subunits of NF-Kappab With a Cell Adhesion Model, Mol. Cell Biol. 13 3802–3810 (1993).
Sokoloski, et al. Antisense Oligonucleotides to the P65 Subunit of NF-Kappa-B Block CD11B Expression And Alter Adhesion Properties of Differentiated HL-60 Granulocytes 82 625–632 (1993).

ANTISENSE OLIGONUCLEOTIDES DIRECTED AGAINST NUCLEIC ACIDS ENCODING NFKB TRANSCRIPTION FACTOR

BACKGROUND OF THE INVENTION

This is a continuation of application Ser. No. 07/950,531 filed Sep. 23, 1992, now abandoned.

Nucleic acid oligodeoxynucleotides complementary to and capable of hybridizing to the sense strand of a gene, or to an mRNA transcribed from that gene, are antisense oligodeoxynucleotides. When the sense strand of a target gene, or an mRNA, is exposed to its antisense oligodeoxynucleotides, hybridization of the two will occur with the result that the gene will be blocked from transcription or the mRNA blocked from translation as long as the oligodeoxynucleotide remains hybridized. Consequently, the protein encoded by the gene (or group of proteins if the gene encodes a regulatory protein) will not be produced. Antisense oligogeoxynucleotides have many uses because of their properties. For example, they are useful for diagnosis by virtue of their ability to bind to target nucleic acids. Also, their effect on protein synthesis makes antisense oligodeoxynucleotides therapeutically useful.

The NF-κB transcription factor complex is a pleiotropic activator which participates in the induction of a wide variety of cellular and viral genes (1,2). The active complex is composed of two subunits designated p50 and p65 (1,3). The genes encoding p50 (4,5) and p65 (6,7) have been cloned and the N-termini of both proteins show considerable homology to the product of the oncogene rel. Numerous cell adhesion molecules, (CAMs), including ICAM-1 (13), vimentin (14), and ELAM-1 (15) have NF-κB binding sites within their 5' regulatory regions. NF-κB may affect cell adhesion by regulating a variety of these adhesion molecules, thus affecting cell growth.

It is possible to use cellular adhesion as an assay for antisense function. For example, inhibition of a putative adhesion molecule and a tumor suppressor gene deleted in colorectal cancer (DCC), by antisense oligodeoxynucleotide, causes detachment of a variety of cells (17).

Cell-to-cell and cell-to-substratum adhesions are mediated through several different families of receptors which target cells toward specific extracellular matrix (ECM) proteins and ligands of adjacent cells (Albelda and Buck, 1990). These receptors also influence diverse aspects of cell growth, differentiation, junction formation, and polarity (Albelda and Buck, 1990; Hynes, 1992). In tissue culture cells, the formation of focal contacts (specialized membrane areas where the cell binds to the ECM) involves proteoglycans such as heparin sulfate, as well as various integrin molecules (Culp et al., 1986; LeBaron et al., 1988). The integrins are heterodimeric molecules that function both as cell-to-substratum and cell-to-cell adhesion receptors (Albelda and Buck, 1990). Adhesion molecules of the immunoglobulin supergene family are also involved in cell-to-cell adhesion. These molecules play an important role in embryogenesis, wound healing, inflammatory response, coagulation, and metastasis (Albelda and Buck, 1990; Hynes 1992).

The recognition that cell adhesion molecules are involved in inflammation has led to novel therapeutic approaches. (Rosen & Gordon 1989). Monoclonal antibodies against specific cell adhesion molecules have been used to inhibit neutrophic recruitment into areas of skin inflammation in septic shock and in ischemia—reperfusion injury.

SUMMARY OF THE INVENTION

It has been found that oligodeoxynucleotides which through substantial hybridization block the production of NF-κB transcription factor by NF-κB genes can be used to prevent cell adhesion. The claimed invention provides a means for preventing cellular adhesion by blocking NF-κB synthesis with antisense oligodeoxynucleotides. In this application, the meaning of the words "oligomer" and "oligo" is defined as oligodeoxynucleotide.

Undifferentiated ES cells were cultured in the presence of p65 oligos (30 µM). The cells were trypsinized and replated onto fibronectin- (10 µg/ml) or laminin- (10 µg/ml) coated dishes and photographed after 72 hours.

Figure 4:
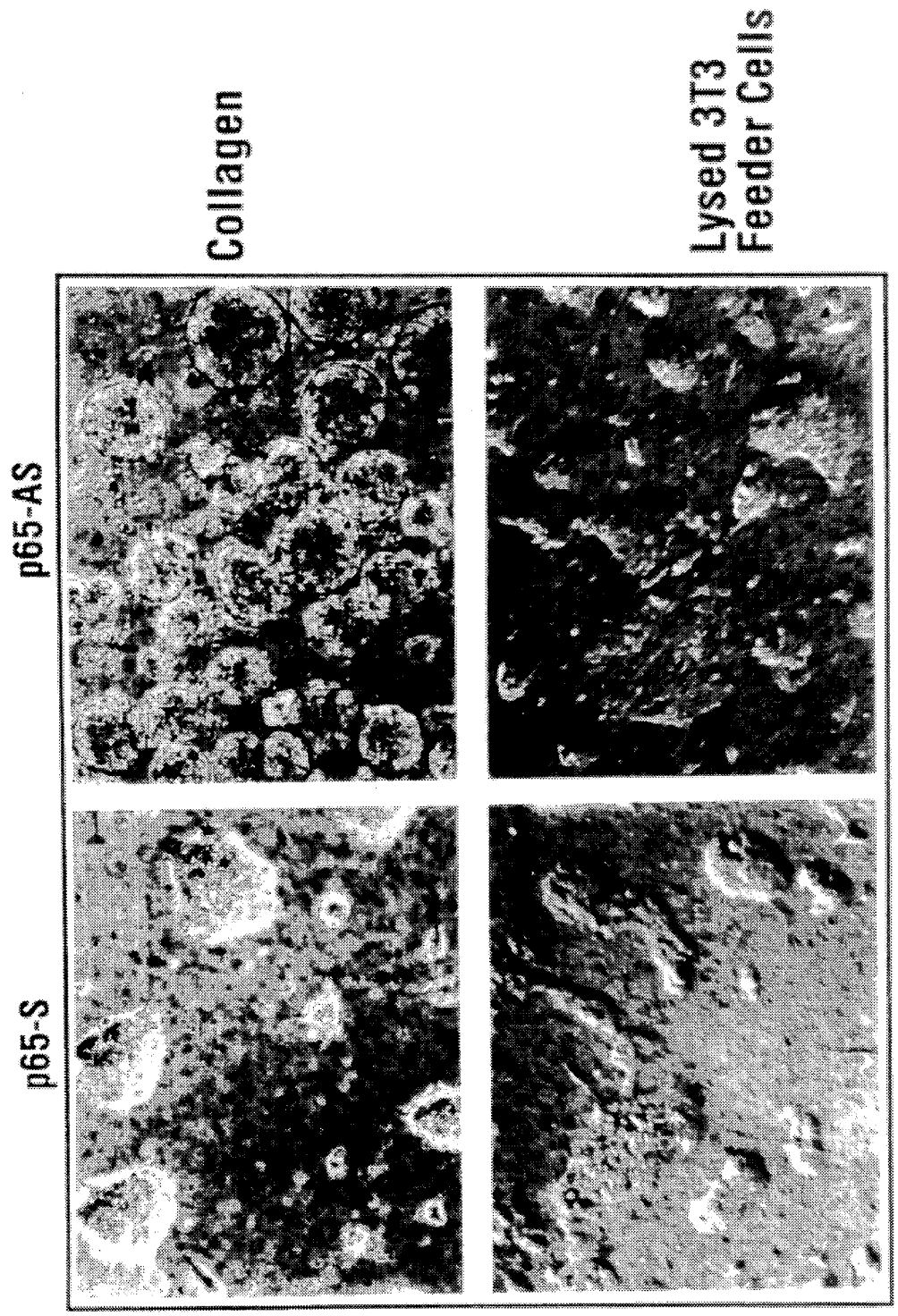

FIG. 4: Abrogation of p65 Antisense Oligos' Effect on Cell Adhesion by ECM From Feeder Layer Fibroblasts Undifferentiated ES cells were cultured in the presence of p65 oligos (30 µM). The cells were trypsinized and replated onto collagen Type IV (5 µg/ml) or onto an ECM generated by lysing the 3T3 feeder cells, and photographed after 72 hours.

Figure 5:
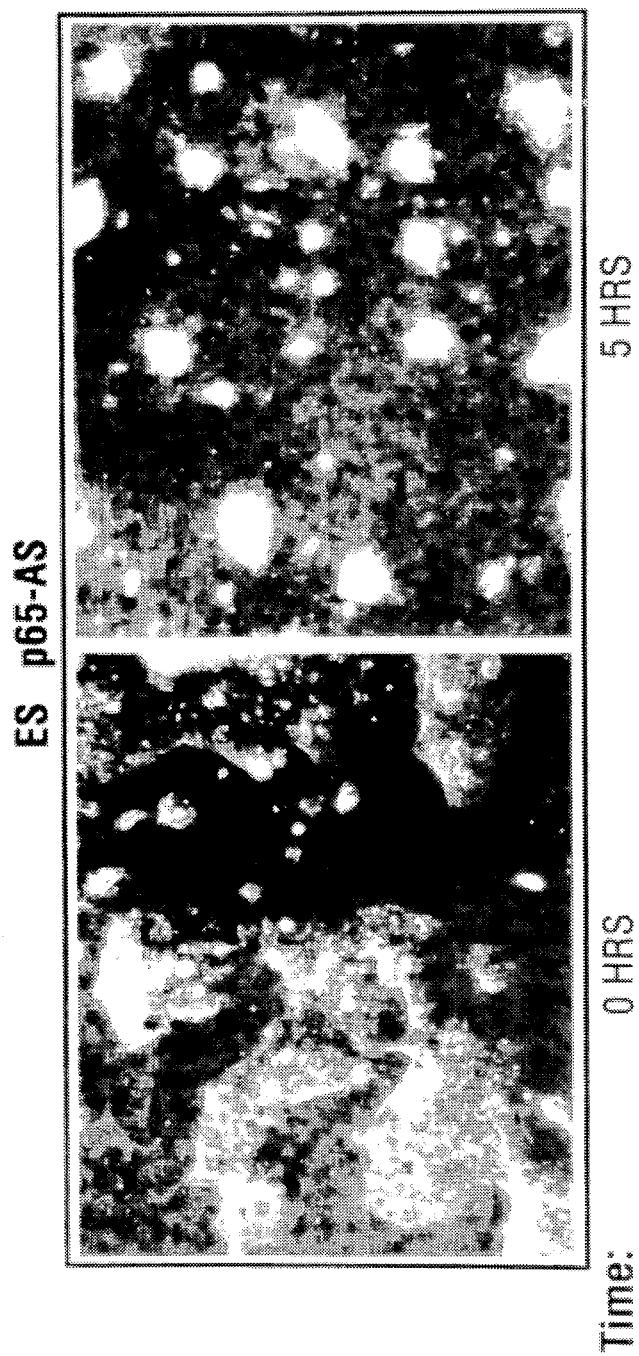

FIG. 5: Rapid Inhibition of ES Cell Adhesion by Antisense Oligos to p65

Undifferentiated ES cells were cultured on gelatin-coated dishes for 72 hours in the absence of oligos. Medium was removed and new medium containing 30 µM of antisense or sense (not shown) p65 was added to the attached cells. An area was marked and photographed immediately (0 time) and after 5 hours.

Figures 6A, 6B:
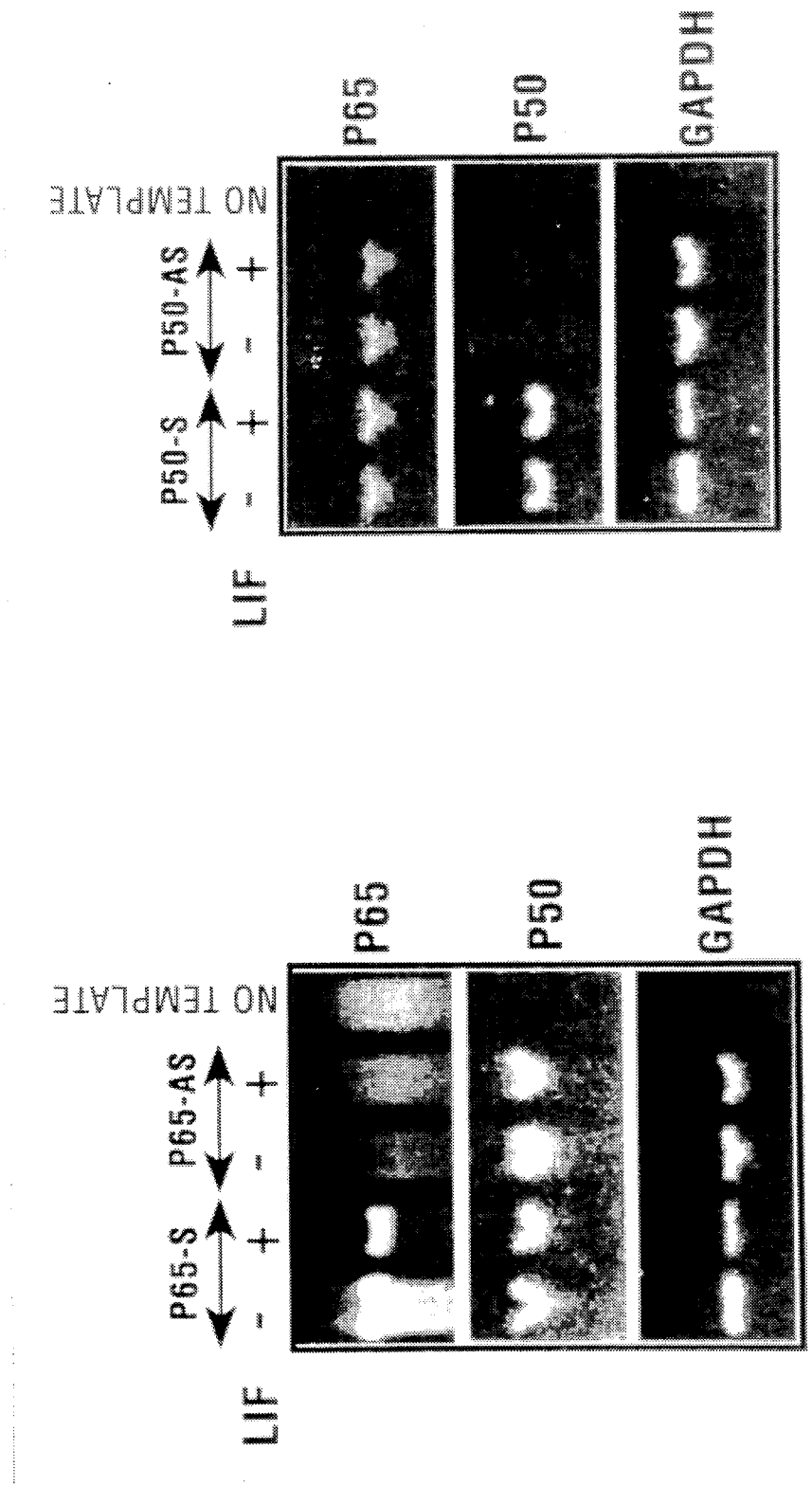

FIG. 6A: Inhibition of p65 mRNA Expression by Antisense Oligos

Undifferentiated and differentiated ES cells were cultured in the presence of p65 thio oligos for 72 hours. Total RNA was isolated and analyzed by RT-PCR for p65, p50, and GAPDH expression.

FIG. 6B: Inhibition of p50 mRNA Expression by Antisense Oligos

Undifferentiated and differentiated ES cells were cultured in the presence of p50 thio oligos for 72 hours. Total RNA was isolated and analyzed by RT-PCR for p65, p50, and GAPDH expression.

Figure 7:
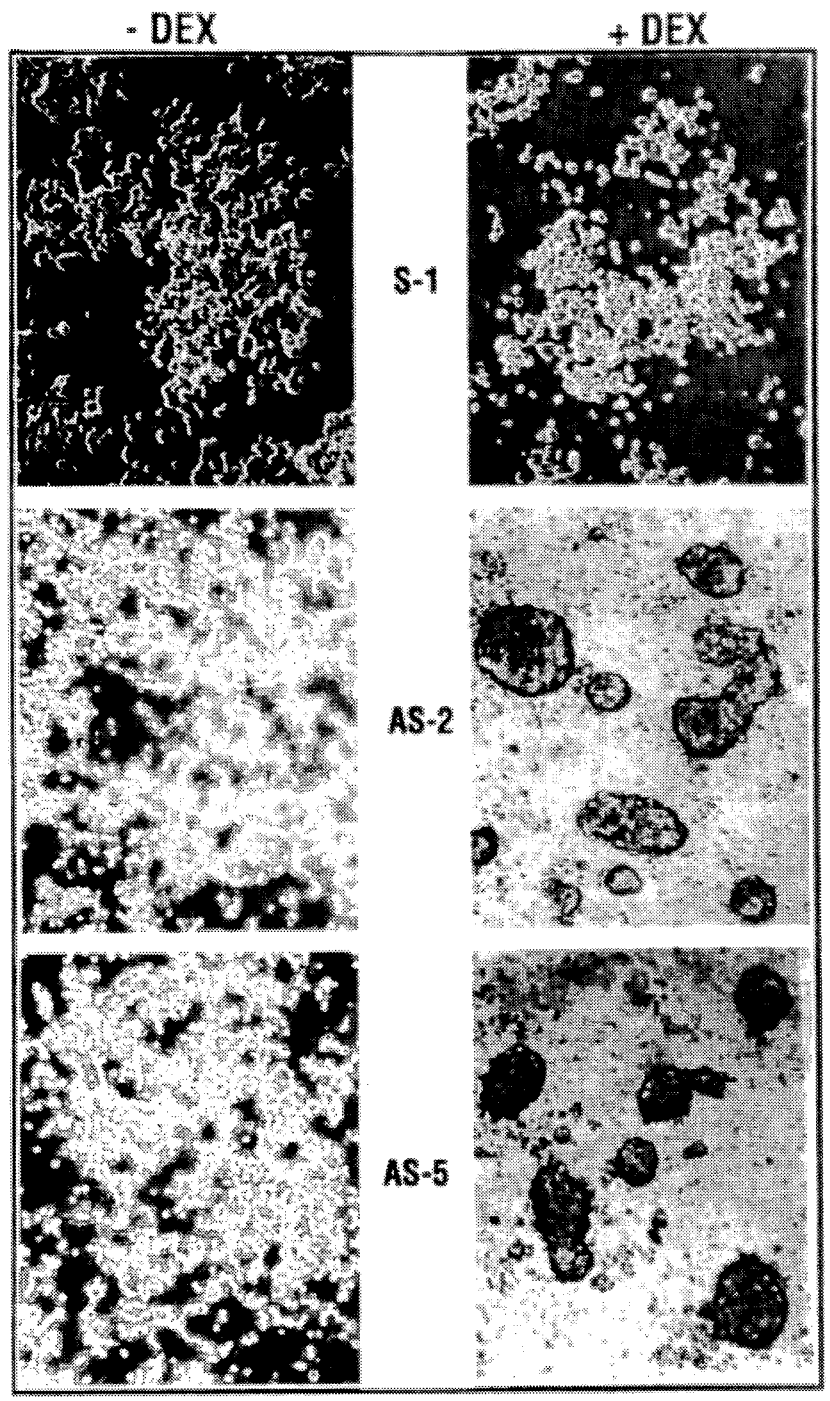

FIG. 7: Inhibition of PC-12 Cells' Adhesion by Inducible Antisense RNA to p65

Four sense clones and eight antisense clones were used in this experiment. Representative clones (S-1, AS-2, and AS-5) are shown. Cells were treated with or without dexamethasone ($1 \times 10^{-6}$ M) for 72 hours, replated, and photographed after 24 hours.

Figure 8:
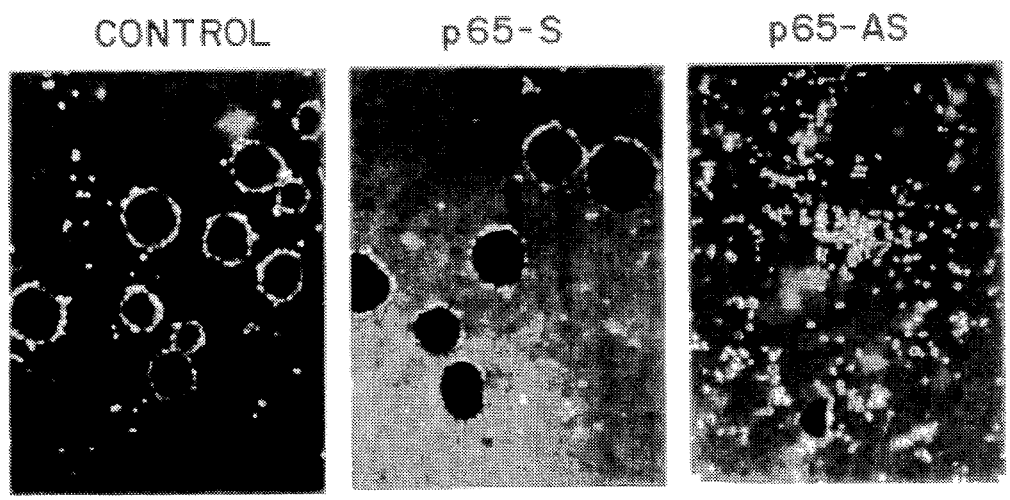

FIG. 8: Inhibition of In Vitro transformation by antisense p65

K-RAS transformed BALB/C 3T3 cells were treated with sense and antisense oligo to p65 and their growth in soft agar was measured at Day 10.

DETAILED DESCRIPTION OF THE INVENTION

In accordance with this invention, any oligomer which is substantially complementary to a portion of the genes encoding the NF-κB transcription factor so as to hybridize with said portion, to substantially prevent production of NF-κB transcription factor by said genes, can be used to prevent cell adhesion. Cell adhesion is an important factor in such conditions as inflammation, wound healing, and tumor development. These oligomers have the therapeutic application of alleviating these conditions.

Oligomers which hybridize with a portion of NF-κB genes to substantially prevent synthesis of NF-κB complex from occurring are useful to prevent cell adhesion. Any oligomer which will bind to these portions of NF-κB genes will prevent NF-κB production as described. When NF-κB production is blocked in a cell exposed to such oligomers, the cell loses its ability to adhere to surfaces. Among the referred portions of the NF-κB gene which when blocked through hybridization substantially prevent NF-κB synthesis from occurring are those having the following sequences or substantially the following sequences: GCC ATG GAC GAA CTG TTC CCC [SEQ ID: 1]; and AGA ATG GCA GAA GAT CCA [SEQ ID: 2].

The claimed oligomers are capable of hybridizing to a portion of a gene (or an mRNA) encoding NF-κB transcription factor. When such an oligomer is hybridized to a portion of NF-κB genes, production of NF-κB by the genes will be substantially prevented. Substantial prevention means that NF-KB is not produced, or is produced at nonfunctional levels. As used herein, binding to a gene is intended to include binding to the corresponding mRNA. NF-κB has two subunits called p50 and p65, encoded by separate genes. Each of these genes is considered to be a gene which encodes NF-κB. The oligomers described herein are capable of binding to either the p50 gene or the p65 gene, in particular the human genes. If either p65 gene or the p50 gene is blocked by hybridization to an oligomer, NF-κB transcription factor will not be produced. The oligomers are substantially complementary to their target sites. They need not reflect the exact sequence of the target site, but must be sufficiently complementary to hybridize selectively to the target site.

Specifically, an oligomer having the sequence GGG GAA CAG TTC GTC CAT GGC [SEQ ID: 3] binds to a portion of the gene encoding the human p65 subunit. An oligomer having the sequence TGG ATC TTC TGC CAT TCT [SEQ ID: 4] binds to a portion of the gene encoding the human p50 subunit.

The preferred oligomer length is about 21 nucleotides, however, lengths of 5 to 50 nucleotides may be used. Higher specificity is a property of longer oligomers, however, this property may be balanced with stability considerations and ease of passage across cell membranes, for which shorter oligomers are preferable.

When an oligomer as disclosed herein is introduced into a cell, the oligomer substantially reduces or prevents NF-κB synthesis by binding to a portion of the NF-κB gene or to NF-κB mRNA. Surprisingly, the cell loses its ability to adhere to a surface as a result. These oligomers therefore are useful as antisense oligomers and prevent cells exposed to them from adhering to surfaces. An oligomer which will block NF-κB synthesis and cell adherence can be selected by cell adhesion assays described in the Examples.

This is surprising for the reason that NF-κB is a transcription factor, therefore it mediates transcription of DNA into mRNA, a function basic to all cells. Blocking the synthesis of NF-κB would be expected to upset a cell's metabolism and damage or kill the cell. Instead, the treated cell survives, but loses its ability to perform a highly specific function namely to adhere to a surface. Loss of adherence prevents cells from adhering to each other or to physiological substrates. Therefore, cells exposed to the oligomers will change their behavior. Since NF-κB is a protein found in cells of all types and tissues, the oligomers disclosed will function to reduce or eliminate adherence in any cell which can adhere to a surface.

Oligomers as claimed may be produced by well-known methods, for example by cloning or by synthesis, and as described in the Examples. Oligomers may be derived from the sequence of a target gene, or from a nucleic acid sequence deduced from the sequence of a protein.

Oligomers produced by any conventional means are screened to determine their ability to substantially prevent NF-κB synthesis. Determination of an oligomer which can hybridize to a portion of genes encoding NF-κB and by so doing substantially prevent NF-κB synthesis by the genes can be accomplished by any conventional method for detecting hybridization and cellular adhesion. A cellular adhesion assay for such screening is described in the Examples. Briefly, cells of any type capable of adherence to a surface may be grown under conventional conditions in for example a culture dish for an amount of time sufficient to permit the cells to adhere to the bottom of the dish (or any appropriate vessel in which cells may be cultured). A layer of gelatin or any other appropriate substrate may be used to coat the dish surface before cells are added. The oligomers are then added to the cells in culture, and after a period of time, the desired effect of the oligomers is observed when the cells detach from the surface of the dish. Twelve to twenty-four hours is a preferred incubation time to observe loss of adherence. However, longer periods of several weeks or more may be needed.

Oligomers which block cell adhesion may be synthesized with modifications to enhance stability. The phosphate groups of the nucleotides which compose the oligomers may be modified such that in the position of the free single-bond oxygen of a natural nucleic acid phosphate, there may be oxygen, methyl, or sulfur. Such modified oligomers are made by conventional synthesis as described in the examples. Any of these substitutions may be made by adding the appropriate molecule to an automatic synthesizer by known methods.

Preferred oligomers have the following structures:

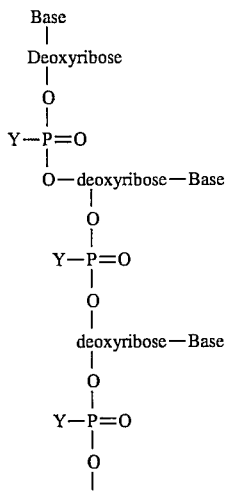

Base represents the nucleotide bases A, T, C, G. Y is selected from O-, or S-, or methyl-.

Preferred modified oligomers are as described above, and have the following base sequences:
GGG GAA CAG TTC GTC CAT GGC [SEQ ID:3] and
TGG ATC TYC TGC CAT TCT [SEQ ID:4]

The claimed oligomers therefore are comprised of nucleotides with sequences provided above and whose nucleotides are connected by phosphate groups of the formula:

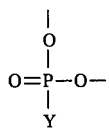

wherein Y is selected from the group consisting of methyl, oxygen, and sulfur.

The claimed oligomers are useful since they prevent cell adhesion. It is this property that gives the oligomers utility, for example, in the treatment of inflammation, to promote wound healing, and to break up tumors by preventing cell adhesion.

For prevention of cell adhesion, the oligomers may be directly injected into the blood-stream or into a target tissue, from either of which entry the oligomers then pass through cell membranes by diffusion or through a receptor and into cells, when they hybridize with the target sequence described above. The oligomers may be associated with targeted carriers such as antibody or receptor fragments, or may be provided by conventional means in liposomes or micelies for more efficient delivery into cells. Modifications as described which provide oligomers with phosphate groups substituted with methyl or sulfur result in oligomers which are stabler against enzymatic degradation and therefore are preferable to unmodified oligomers of the same sequence for treatment purposes. In addition, modified oligomers may pass more easily through cell membranes than unmodified oligomers.

Any conventional method for delivery of a biologically active compound may be used to deliver an effective amount of oligomer. More specifically oligomers modified or unmodified may be delivered alone, or in composition with a suitable pharmaceutical carrier or coupled with carriers. Examples of carriers, include peptides, immunoglobulins and their fragments, liposomes, receptor molecules, ligand molecules such as hormones, enzymes, and any conventional compounds for pharmaceutical administration.

Delivery of an effective amount of oligomer may be oral, parenteral, intravenous, or dermal or by any conventional pharmaceutical route. Conventional formulations for such administration, including an effective amount of oligomer, are part of this invention. Oligomers may be applied topically to prevent cell adhesion in target issues.

An effective amount of oligomer may be determined by one skilled in the art on the basis of experimental data. For example, effective amounts at site of treatment may be determined from in vitro studies providing effective amounts for individual cells. These amounts may be extrapolated to provide for cell mass at treatment site, and to account for reductions in effective concentration due to failure of some fraction of oligomer to reach the treatment site. The oligomer concentration will depend on various known factors. These include stability of the oligomer based on its length, modification, and carrier, route of administration and vehicle of administration, (oral, dermal, parenteral, or intravenous), and site of treatment, which determines physiological barriers such as the blood-brain barrier. The condition being treated is also a consideration.

A preferred effective amount of oligomer at the treatment site is from about $1\times10^{-8}$M to about $1\times10^{-5}$M. In a topical composition, the preferred effective amount of oligomer is in a solution, emulsion, cream or ointment with a pharmaceutically acceptable carrier.

Pharmaceutical vehicles include solutions, ointments, tablets, and any conventional vehicle appropriate to a given mode of delivery. A solution or ointment is preferred. A solution may include in addition to oligomers and/or salts thereof, buffers such as saline, stabilizers, such as BSA, and other conventional components. Ointments, creams, emulsions, lotions and shampoos all intended for topical application include well-known components.

The oligomers of the invention may be used to treat conditions related to cell adhesion.

Inflammation is mediated by cellular adherence to substrates and other cells. Therefore, prevention of cell adherence would reduce local inflammation. Therefore, a method of treating inflammation comprises administering to a patient an amount of the claimed oligomers sufficient to reduce the inflammation. A preferred effective concentration of oligomer is about $1\times10^{-8}$M to about $1\times10^{-5}$M at the inflammation site. A preferred made of adminstration is topical administration. Wound healing is also affected by cell adhesion. Therefore, the claimed oligomers may be administered for wound healing purposes exactly the same way as described for inflammation.

The claimed oligomers are also useful to break up solid tumors. Cell transformation is frequently associated with qualitative alteration in the integrin repertoire (37). The mechanism of tumor invasion and metastasis involves complex changes in normal cell-to-cell and cell-to-substratum interactions (38–41). The process of tumor progression is complex and requires malignant cells to display both decreased and increased adhesion properties at various times in the development of the tumor (39,42,43).

For tumor cells to metastasize, the tumor cells must first attach to the extracellular matrix of a blood vessel. The claimed oligomers inhibit adhesion of cells to the matrix. Therefore, treatment with the oligomers would prevent component cells of the tumor from adhering to each other, thus dissolving the tumor. The nonadherent tumor cells will then be removed by the immune system. Also, the nonadherent tumor cells cannot cause metastasis because they cannot attach, and may revert back to a normal phenotype with no tumorogenic potential. Therefore, the claimed oligomers may be used in a method for treating solid tumors which comprises administration an amount of the claimed oligomers sufficient to cause dissolution of the solid tumor. The solid tumor may be a metastatic tumor.

This invention is illustrated by the following examples, which are not intended to limit the invention in any way.

EXAMPLES

Method 1: Antisense Oligonucleotides

The thio analogs of the oligonucleotides were synthesized using an automated synthesizer (model 394, Applied Biosystems, Foster City, Calif.), according to published protocol (16). The oligomers were purified as described (17) with one modification: the oligos were routinely re-extracted with ether (6 times) before washing with absolute ethanol. Cells were trypsinized, mixed with the oligos (30 μM), and plated onto a variety of ECM-coated dishes as previously described (18) for 24 hours to 2 weeks; in some experiments the oligos were added every 48 hours. In some experiments, cells were also plated first and allowed to attached before addition of the oligos. The antisense oligo experiments were repeated 3 to 4 times with independently prepared oligos. Cells were used at different passages.

Method 2: Cell Culture

The ES cells (CCE-24, L. Robertson, Columbia University) were routinely grown on 1% gelatin-coated dishes in Dulbecco's Modified Eagle's Medium (DMEM) containing 15% heat-inactivated fetal bovine serum (FBS), 10 ng/ml of human leukemia inhibitory factor (LIF) (UBI, Lake Placid, N.Y.), and monothioglycerol (Sigma, St. Louis, Mo.) at $4.5 \times 10^{-4}$M. Differentiation was initiated by the removal of LIF and subsequent subculturing for 6 to 8 days in medium minus LIF. The cell lines NIH 3T3, Rat-1, PC-12, and S-17 were maintained as described (17,19). Primary human vascular endothelial cells (HUVECs) and primary keratinocytes were from Clonotech Inc., Palo Alto, Calif. RHEK-1 cells were maintained as described (20). An extracellular matrix (ECM) was established from feeder layer fibroblasts by lysing the confluent cultures with 0.5% triton X-100 containing $3.5 \times 10^{-4}$M $NH_4OH$ for 5 minutes at room temperature followed by three washes with phosphate-buffered saline (PBS).

Method 3: PCR Analysis

RT-PCR was performed as previously described (17). The p65 primers (1) 5' GCG GCC AAG CTT AAG ATC TGC CGA GTA AAC 3' [SEQ ID: 5] and (2) 5' CGC TGC TCT AGA GAA CAC AAT GGC CAC TTG CCG 3' [SEQ ID: 6] define an amplicon of 150 bp. The p50 primers (1) 5' AAA GGT TAT CGT TCA GTT 3'[SEQ ID: 7] and (2) 5' TTG TAG ATA GGC AAG GTC 3' [SEQ ID: 8] define an amplicon of 250 bp. The GAPDH primers have been described (17). The cytokine receptor primer sequences have been described (21).

Method 4: Plasmid Construction

A 350 bp fragment of m-p65 cDNA was cloned by RT-PCR from NIH 3T3 cell cDNA, encompassing the ATG initiation codon. The PCR primers include (1) 5' ACC GCT CGA GCT AGC CGG GGA CCC TGA CCA TGG AC 3' [SEQ ID: 9] and (2) 5' CCG GAA TTC GCT AGC GCT TCA CAC ACT GGA TCC CCA GG 3' [SEQ ID: 10] and the amplified fragment was inserted into the NheI site of the MAM-Neo-CAT vector (17). Sense and antisense clones were characterized by restriction analysis and confirmed by sequencing. Supercoiled plasmid DNAs were transfected onto PC-12 cells by electroporation as described (19).

Methods 5: RNA Isolation

RNA was isolated by RNAzol-B (Cinna Biotecx, Friendswood, Tex.). Northern blot was performed as previously described (17).

EXAMPLE 1

Figure 1:
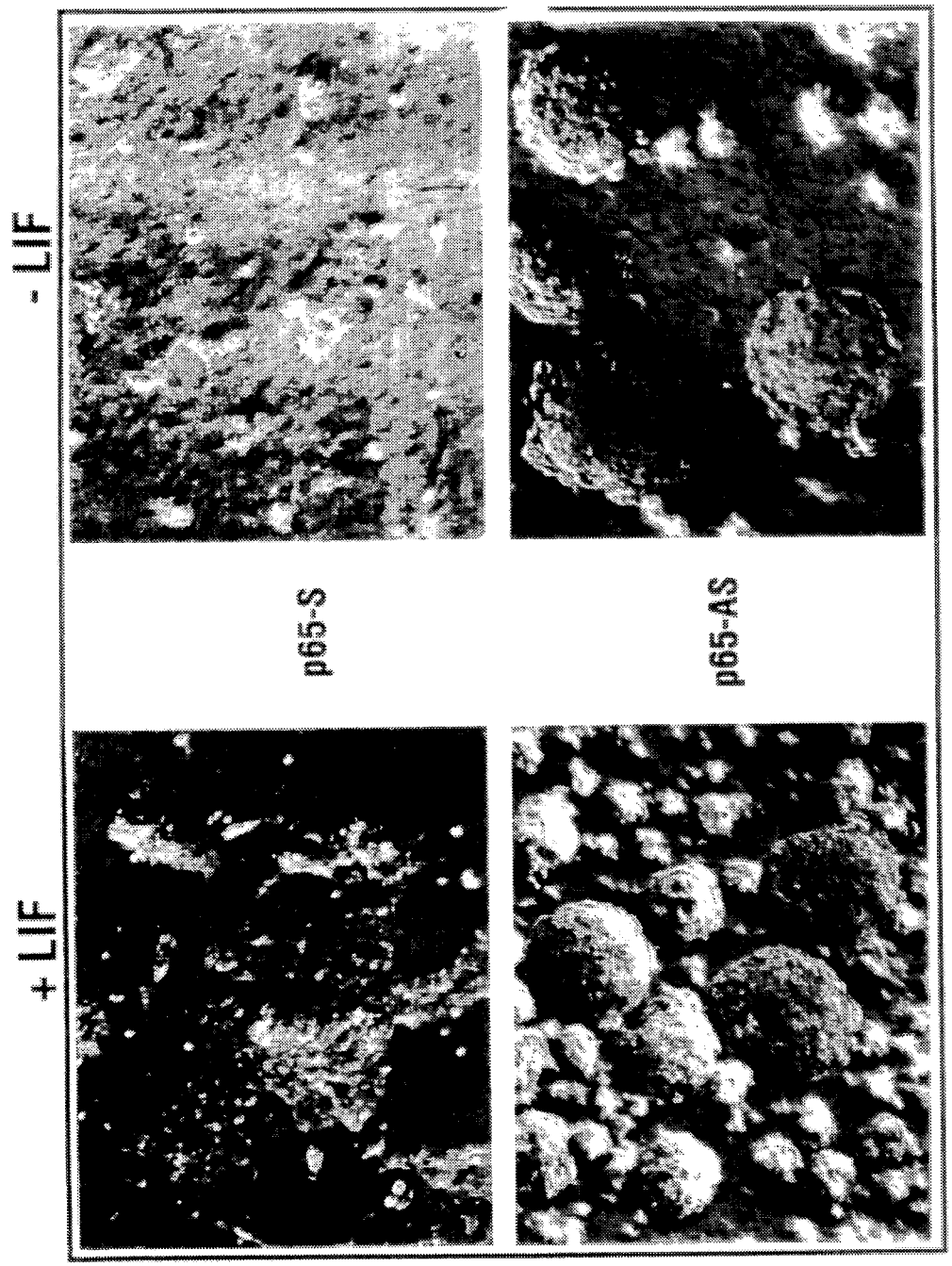
FIG. 1: Antisense Oligos to p65 Inhibit ES Cell Adhesion to a Matrix Independent of Differentiative Status ES cells were cultured differentiated and undifferentiated as described in Materials and Methods. Cells were trypsinized and mixed with oligos to p65 (30 µM), replated onto gelatin-coated dishes, and photographed after 72 hours in culture.

A cellular adhesion assay demonstrates the effects of the claimed oligomers. Modified phosphoro-thio oligonucleotides to the individual subunits of NF-κB were synthesized (Table 1). Murine ES cells were used to test the effects of inhibition of the p50 and p65 subunits of NF-κB. The ES cells were maintained undifferentiated by the presence of leukemia inhibitory factor (LIF); differentiation was initiated by withdrawing LIF from this culture. Exposure of both the differentiated and undifferentiated ES cells to p65 antisense oligos caused complete detachment of the cells from the gelatin-coated dishes; the control (sense) p65 oligo had no effect on the ES cells' adhesion (FIG. 1).

Figure 2:
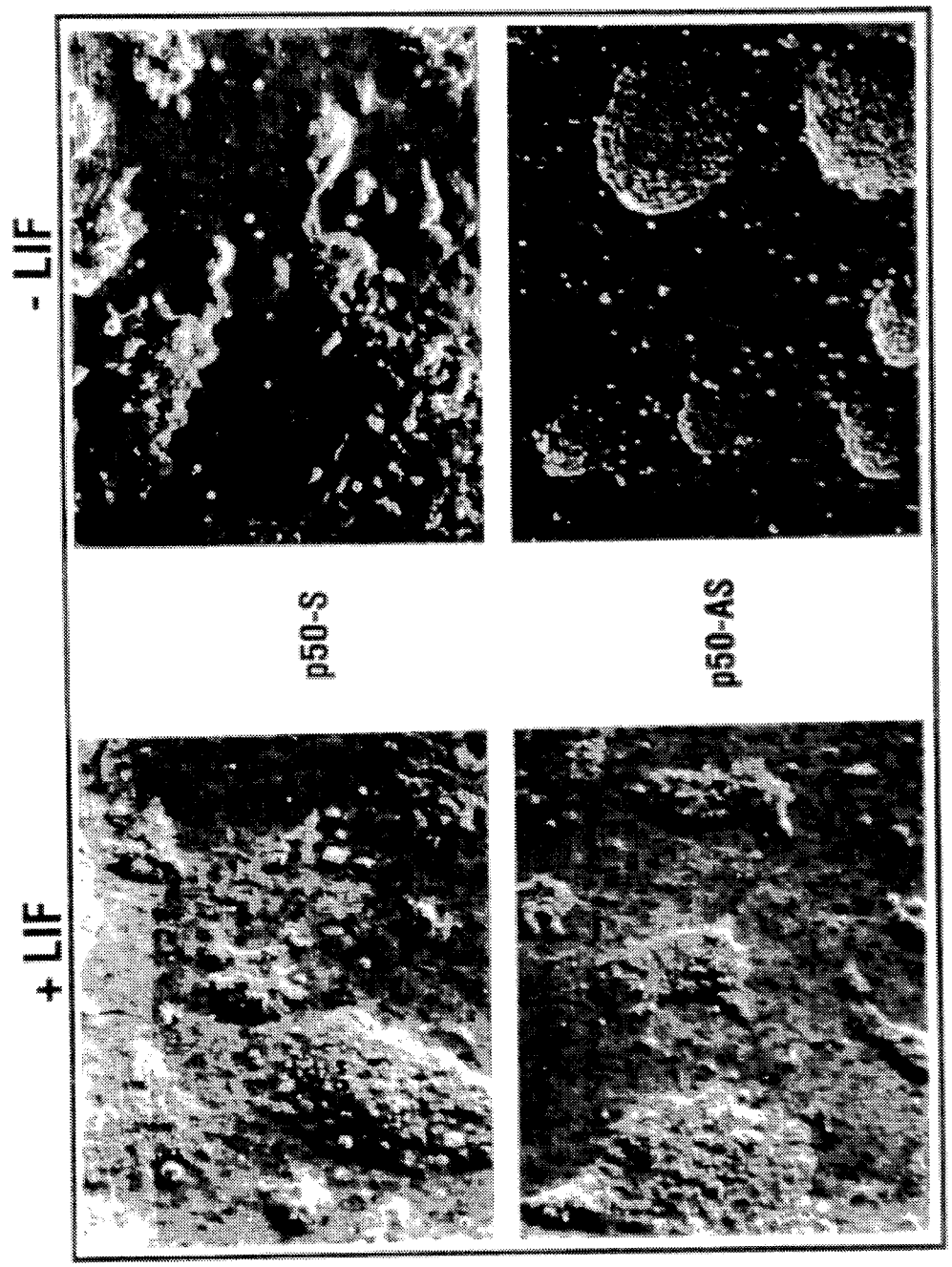
FIG. 2: Differentiation-Specific Inhibition of ES Cell Adhesion by p50 Antisense ES cells were cultured on gelatin-coated dishes and allowed to differentiate for six days by withholding LIF. The trypsinized cells were then mixed with the oligos to p50 (30 µM) and plated onto gelatin-coated dishes and photographed as in FIG. 1.

The p50 antisense oligos exhibited a dramatic effect dependent on the differentiational status of the ES cells: in the undifferentiated ES cells, the p50 antisense oligos had no effect. After removal of LIF for six days to allow the ES cells to differentiate, addition of p50 antisense oligos caused complete detachment of cells, an effect identical to that of p65 antisense oligos (FIG. 2). The differentiative status of these ES cells was confirmed by monitoring the upregulation of diverse cytokine receptors such as epo-R, c-kit, G-CSF-R, and CSF-1R. The antisense oligo-detached cells were determined viable by trypan blue exclusion and continued to grow in the presence of antisense oligos (oligos being replaced every 48 hours) for two to three weeks. The effect of these antisense oligos on ES cell adhesion is highly specific and is not due to a nonspecific toxicity. Several unrelated antisense oligos had no such effect on ES cell adhesion. The antisense oligo-treated ES cells grew as an aggregate in suspension, similar to ES cell growth in methyl cellulose cultures (22). Furthermore, the effects of antisense p50 and p65 were transient; when replated in the absence of new oligos, the antisense oligo-treated ES cells retained their differentiated or undifferentiated morphology. These results indicate that NF-κB plays an important role in cell-to-substratum adhesion, such that preventing NF-κB from functioning disables cell adhesion.

EXAMPLE 2

Figure 3:
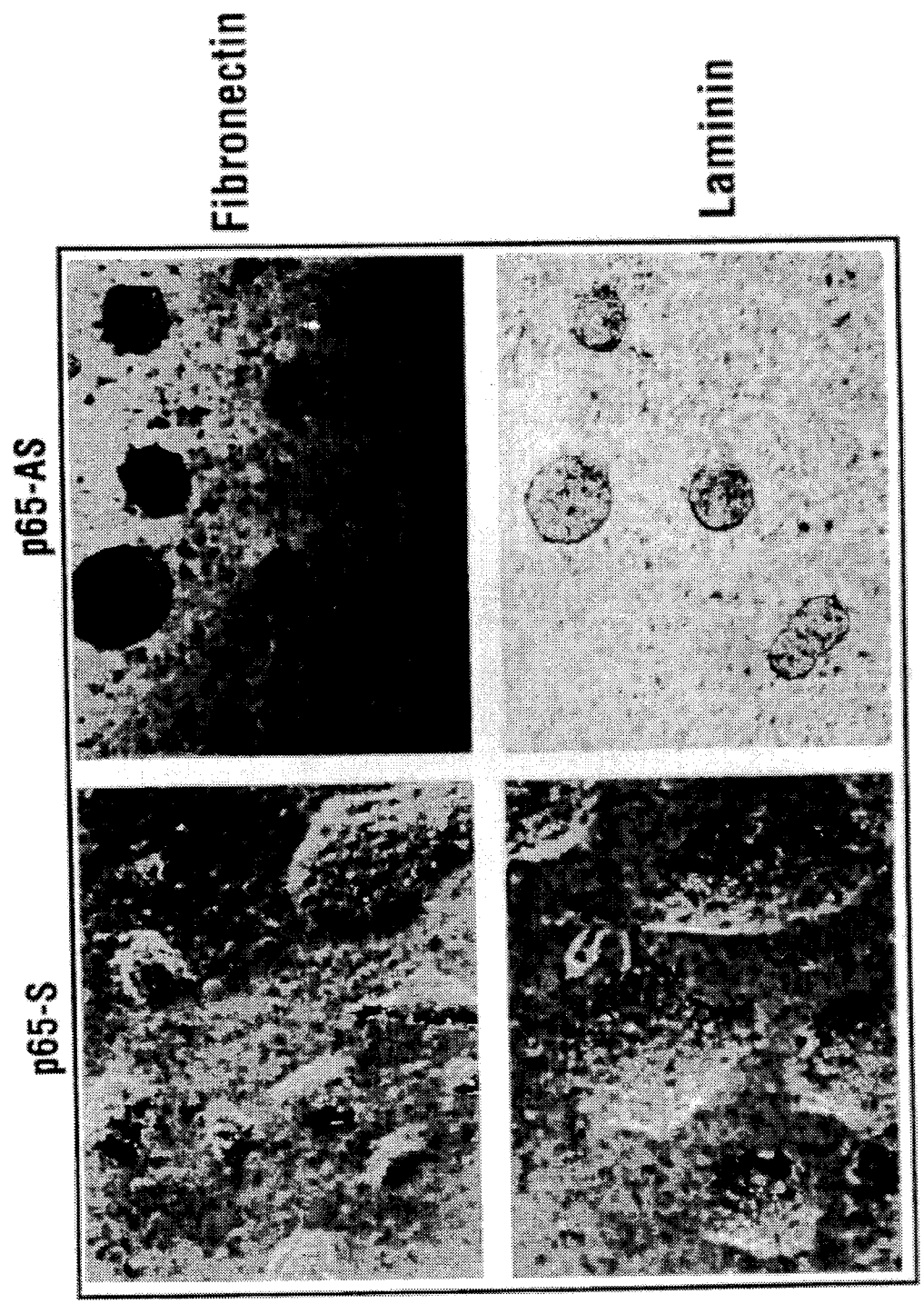
FIG. 3: Effect of ECMs on p65 Antisense-Mediated Inhibition of Cell Adhesion

ES cells plated on fibronectin, laminin, or collagen were completely detached when exposed to p65 antisense oligos. However, when the ES cells were plated on an ECM generated by lysed feeder-layer cells (FIGS. 3, 4), the detachment effect of p65 antisense oligos was completely abolished. Some other adhesion molecule(s) is provided by the total ECM from feeder cells, independent of NF-κB function.

The effect of p65 antisense oligos on ES cell adhesion is very rapid: within 5 hours, the p65 antisense-treated cells showed dramatic alteration in their adhesion property (FIG. 5). These cells were completely detached within twelve to fourteen hours, whereas neither the p65 sense nor the p50 antisense oligos had any effect on the adhesion of undifferentiated ES cells for up to two weeks.

RT-PCR shows that the p65 antisense oligos abolished p65 mRNA expression in both the undifferentiated and differentiated ES cells, while the expression of p50 and that of a housekeeping enzyme, GAPDH, was unaffected in these cells (FIG. 6A). Similarly, the p50 antisense oligos inhibited p50 mRNA expression regardless of the differentiative status of the ES cells, whereas the p65 or GAPDH mRNA expression was not affected in these cells (FIG. 6B). These results indicate that the differential effects of p65 vs. p50 antisense oligos on ES cell adhesion is due to selective inhibition of the respective mRNA expression.

The p65 antisense oligos caused complete detachment of diverse cell lines and primary cells, effects that were sequence and species specific. p50 antisense had no effect on these cells. These results strongly support a pleiotropic function for NF-κB and a more specific role in cell adhesion for the p65 subunit of NF-κB.

EXAMPLE 3

To corroborate the effects of antisense oligos to p65 on cell adhesion, a stable PC-12 cell line expressing dexamethasone-inducible antisense RNA to p65 utilizing a MAM-Neo-CAT vector (17,19) and established both control (sense) and antisense transfectants of PC-12 cells was used. High levels of dexamethasone-inducible antisense RNA to p65 were detected in several independent clones. The control sense clones showed no change in cell adhesion properties when treated with dexamethasone (FIG. 7), and the antisense p65 clones showed a normal morphology in the absence of dexamethasone. However, dexamethasone induction of antisense RNA to p65 caused a dramatic effect on cell adhesion to the substratum similar to the effect of antisense oligos to p65 in these cells. Following the removal of dexamethasone from these antisense clones, the cells reverted to normal morphology.

The inhibition of cell adhesion by p65 antisense oligos was applicable to diverse cell types tested, supporting a pleiotropic requirement of NF-κB complex for cell adhesion. Individual ECMs such as fibronectin, laminin, or collagen could not overcome the requirement of CAMs regulated by NF-κB function. However, ECMs generated by feeder layer cell lysates had the ability to supplement the requirement of NF-κB function in cell adhesion. This raises the possibility that NF-κB independent CAMs also are involved in cell adhesion.

A dexamethasone-dependent inhibition of cell adhesion to the substratum was seen in stable PC-12 antisense transfectants which expressed high levels of inducible antisense RNA to p65. The antisense oligos as well as antisense RNA to p65 caused the PC-12 cells to grow detached from the substratum as aggregates. Inhibition of p65 expression may interfere with cell-to-substratum, rather than cell-to-cell, adhesion in these cells.

Inhibition of p50 mRNA by p50 antisense oligos had no effect on diverse cell types except in the ES cell system, where a dramatic effect was seen. The adhesion of undifferentiated ES cells was not affected by inhibition of p50 expression, but in differentiated ES cells, inhibition of p50 mRNA resulted in pronounced inhibition of adhesion, identical to the effects of p65 antisense. These results indicate that in differentiated ES cells the p65 subunit of NF-κB can either complex with some subunit other than p50 or can function as a homodimer. This is further supported by our observations that inhibition of p65 expression alone in diverse cell types, can elicit a dramatic effect on cell adhesion. Under these conditions p50 expression was not affected. Thus in normal cells, p65 can play an essential function in regulating diverse genes involved in cell adhesion and can not exist solely complexed with cytosolic inhibitory protein IκB (11).

EXAMPLE 4

Malignant cells show decreased adhesion during the progression of tumors (39, 42, 43). Inhibition of NF-κB by antisense p65 inhibits tumor cell growth. In vitro results showed that in Ras—transformed cells, the transformed phenotype is inhibited by the use of antisense oligos to p65 (FIG. 8). In vivo stable antisense RNA expressing cell lines utilizing a dexamethasone inducible vector (described in Example 3) were used to demonstrate tumor inhibition. These antisense RNA expressing clones were injected into nude mice, and the mice were treated with or without dexamethasone. The antisense clones showed complete lack of tumor formation when treated with dexamethasone. In addition, the tumor bearing mice from the antisense clones maintained in the absence of dexamethasone, showed complete regression of tumor within a week after dexamethasone treatment.

REFERENCES

40. Albelda, S. M., and C. A. Buck. 1990. Integrins and Other Cell Adhesion Molecules. FASEB J. 4: 2868–2880.
11. Baeuerle, P. A., and D. Baltimore. 1988. IκB: A Specific Inhibitor of the NFKB Transcription Factor. Science 242: 540–546.
1. Baeuerle, P. A., and D. Baltimore. 1989. A 65 kD Subunit of Active NF-κB Is Required for Inhibition of NF-κB. Genes Dev. 3: 1689–1698.
9. Ballard, D., E. Dixon, N. Peffer, H. Bogerd, S. Doerre, B. Stein, and W. Greene. 1992. The 65-kDa Subunit of Human NF-κB Functions as a Potent Transcriptional Activator and a Target for v-Rel-Mediated Repression. Proc. Natl. Acad. Sci. USA 89: 1875–1879.
44. Ballard, D. W., W. H. Walker, S. Doerre, P. Sisra, J. A. Molitor, E. P. Dixon, N. J. Peffer, M. Hannink, and W. C. Greene. 1990. The v-tel Oncogene Encodes a κB Enhancer Binding Protein That Inhibits NF-κB Function. Cell 63: 803–814.
30. Caracciolo, D., M. Valtieri, D. Venturelli, C. Peschle, A. M. Gewirtz, and B. Calabretta. 1989. Lineage-Specific Requirement of c-abl Function in Normal Hematopoiesis. Science 245: 1107–1110.
36. Chiang, M. -Y., H. Chan, M. A. Zounes, S. M. Freier, W. F. Lima, and C. F. Bennett. 1991. Antisense Oligonucleotides Inhibit Intercellular Adhesion Molecule 1 Expression by Two Distinct Mechanisms. J. Biol. Chem. 266: 18162–18171.
35. Daar I. O., and L. E. Maquat. 1988. Premature Translation Termination Mediates Triosephosphate Isomerase mRNA Degradation. Mol. Cell. Biol. 8: 802–813.
43. Edelman, G. M., and K. L. Crossin. 1991. Cell Adhesion Molecules: Implications for a Molecular Histology. Annu. Rev. Biochem. 60: 155–190.
42. Edelman, G. M., B. A. Murray, R. -M. Mege, B. A. Cunningham, and W. J. Gallin. 1987. Cellular Expression of Liver and Neural Cell Adhesion Molecules After Transfection With Their cDNAs Results in Specific Cell-Cell Binding. Proc. Natl. Acad. Sci. USA 84: 8502–8506.
29. Eder, P. S., and J. A. Walder. 1991. Ribonuclease H. From K562 Human Erythroleukemia Cells: Purification, Characterization, and Substrate Specificity. J. Biol. Chem. 266: 6472–6479.
24. Fujita, T., G. Nolan, S. Ghosh, and D. Baltimore. 1992. Independent Modes of Transcriptional Activation by the p50 and p65 Subunits of NF-κB. Genes Dev. 6: 775–787.

4. Ghosh, S., A. M. Gifford, L. B. Riviere, P. Tempst, G. P. Nolan, and D. Baltimore. 1990. Cloning of the p50 DNA Binding Subunit of NF-κB: Homology to Rel and Dorsal. Cell 62: 1019–1029.

3. Ghosh, S., and D. Baltimore. 1990. Activation in vitro of NF-κB by Phosphorylation of Its Inhibitor I-kappa-B. Nature (London) 344: 6789–6829.

26. Goodchild, J. 1989. Inhibition of Gene Expression By Oligonucleotides, p. 53. In J. S. Cohen (ed.), Oligodeoxynucleotides: Antisense Inhibitors of Gene Expression, CRC Press, Boca Raton, Fla.

27. Helene, C., and J. J. Toulme. 1990. Specific Regulation of Gene Expression By Antisense, Sense and Antigene Nucleic Acids. Biochim. Biophys. Acta Gene Struct. Expression 1049: 99–125.

41. Hynes, R. O. 1992. Integrins: Versatility, Modulation, and Signaling in Cell Adhesion. Cell 69: 11–25.

18. Ito, E., J. L. Sonnenberg, and R. Narayanan. Nerve growth factor-induced differentiation in PC-12 cells is blocked by fos oncogene. 1989. Oncogene 4: 1193–1199.

38. Juliano, R. 1987. Membrane Receptors for Extracellular Matrix Macromolecules: Relationship to Cell Adhesion and Tumor Metastasis. Biochim. Biophys. Acta 907: 261–278.

5. Kieran, M., V. Blank, F. Logeat, J. Vandekerchove, F. I. Lottspeich, O. LeBail, M. B. Urban, P. Kourilsky, P. A. Baeuerle, and A. Israel. 1990. The DNA Binding Subunit of NF-κB Is Identical to Factor KBF1 and Homologous to the Rel Oncogene Product. Cell 62: 1007–1018.

23. Kretzschmar, M., M. Meisterernst, C. Scheidereit, G. Li, and R. Roeder. 1992. Transcriptional Regulation of the HIV-1 Promoter by NF-κcB in vitro. Genes Dev. 6: 761–774.

8. Kunsch, C., S. M. Ruben, and C. A. Rosen. Selection of Optimal κB/Rel DNA Binding Motifs: Interaction of Both Subunits of NF-κB With DNA Is Required for Transcriptional Activation. Mol. Cell. Biol. (In Press: MCB# 684-92.)

19. Lawlor, K., and R. Narayanan. Persistent Expression of the Tumor Suppressor Gene DCC Is Essential for Neuronal Differentiation. Cell Growth Differen. (in press).

2. Lenardo, M. J., and D. Baltimore. 1989. NF-κB: A Pleiotropic Mediator of Inducible and Tissue-Specific Gene Control. Cell 58: 227–229.

14. Lilienbaum, A., M. Duc Dodon, C. Alexandre, L. Gazzolo, and D. Paulin. 1990. Effect of Human T-Cell Virus type I TAX Protein on Activation of the Human Vimentin Gene. J. Virol. 64: 256–263.

31. Maier, J. A. M., P. Voulalas, D. Roeder, and T. Maciag. 1990. Extension of the Life-Span of Human Endothelial Cells by an Interleukin-1α Antisense Oligomer. Science 249: 1570–1574.

28. Masutani, C., T. Enomoto, M. Suzuki, F. Hanaoka, and M. Ui. 1990. DNA Primase Stimulatory Factor From Mouse FM3A Cells Has an RNase H Activity. J. Biol. Chem. 265: 10210–10216.

16. Matsukura, M., K. Shinozuka, G. Zon, H. Mitsuya, M. Reitz, J. S. Cohen, and S. Broder. 1987. Phosphorothioate Analogs of Oligodeoxynucleotides: Inhibitors of Replication and Cytopathic Effects of Human Immunodeficiency Virus. Proc. Natl. Acad. Sci. USA 84: 7706–7710.

34. Mullner, E. W., and L. C. Kuhn. 1988. A Stem-Loop in the 3' Untranslated Region Mediates Iron-Dependent Regulation of Transfertin Receptor mRNA Stability in the Cytoplasm. Cell 53: 815–825.

17. Narayanan, R., K. G. Lawlor, R. Q. J. Schaapveld, K. R. Cho, B. Vogelstein, P. Bui-Vinh Tran, M. P. Osborne, and N. T. Telang. 1992. Antisense RNA to the Putative Tumor-Suppressor Gene DCC Transforms Rat-1 Fibroblasts. Oncogene 7: 553–561.

6. Nolan, G. P., S. Ghosh, H. C. Liou, P. Tempst, and D. Baltimore. 1991. DNA Binding and IκB inhibition of the cloned p65 subunit of NF-κB, a rel Related Polypeptide. Cell 64: 961–969.

37. Plantefaber, L. C., and R. O. Hynes. 1989. Changes in Integrin Receptors on Oncogenically Transformed Cells. Cell 56: 281–290.

20. Rhim, J. S., J. Fujita, P. Arnstein, and S. A. Aaronson. 1986. Neoplastic Conversion of Human Keratinocytes by Adenovirus 12-SV40 Virus and Chemical Carcinogens. 1986. Science 232: 385–388.

7. Ruben, S., P. J. Dillon, R. Schreck, T. Henkel, C. -H. Chen, M. Maher, P. A. Baeuerle, and C. A. Rosen. 1991. Isolation of a Rel-Related Human cDNA That Potentially Encodes the 65-kD Subunit of NF-κB. Science 251: 1490–1493.

10. Ruben, S. M., R. Narayanan, J. F. Klement, C. -H. Chen, and C. Rosen. 1992. Functional Characterization of the NF-κB p65 Transcriptional Activator and an Alternatively Spliced Derivative. Mol. Cell. Biol. 12: 444–454.

39. Ruoslahti, E., and F. G. Giancotti. 1989. Integrins and Tumor Cell Dissemination. Cancer Cells 1: 119–126.

33. Sburlai, A. R., R. E. Manrow, and S. L. Berger. 1991. Prothymosin α Antisense Oligomers Inhibit Myeloma Cell Division. Proc. Natl. Acad. Sci. USA 88: 253–257.

21. Schmitt, R. M., E. Bruyns, and H. R. Snodgrass. 1991. Hematopoietic Development of Embryonic Stem Cells In Vitro: Cytokine and Receptor Gene Expression. Genes Der. 5: 728–740.

32. Segal, G. M., T. D. Smith, M. C. Heinrich, F. S. Ey, and G. C. Bagby, Jr. 1992. Specific Repression of Granulocyte-Macrophage and Granulocyte Colony-Stimulating Factor Gene Expression in Interleukin-1-Stimulated Endothelial Cells With Antisense Oligodeoxynucleotides. Blood 80: 609–616.

12. Urban, M. B., and P. A. Baeuerle. 1990. The 65-kD Subunit of NF-κB is a Receptor for IκB and a Modulator of DNA-Binding Specificity. Genes Dev. 4: 1975–1984.

25. van der Krol, A. R., J. N. M. Mol, and A. R. Stuitje. 1988. Modulation of Eukaryotic Gene Expression by Complementary RNA or DNA Sequences. BioTechniques 6: 958–976.

13. Voraberger, G., R. Schafer, and C. Stratowa. 1991. Cloning of the Human Gene for Intercellular Adhesion Molecule I and Analysis of Its 5' Regulatory Region: Induction by Cytokines and Phorbal Ester. J. Immunol. 147: 2777–2786.

15. Whelan, J., P. Ghersa, R. H. van Huijsduijnen, J. Gray, G. Chandra, F. Talabot, and J. F. DeLamorter. 1991. An NF-κB Like Factor Is Essential But Not Sufficient for Cytokine Induction of Endothelial Leukocyte Adhesion Molecule I (ELAM-1) Gene Transcription. Nucleic Acids Res. 19: 2645–2653.

22. Wiles, M. V., and G. Keller. 1991. Multiple Hematopoietic Lineages Develop From Embryonic Stem (ES) Cells in Culture. Development 111: 259–267.

TABLE LEGENDS

TABLE I. Phosophoro-thio Oligos Used in the Study

The oligonucleotide sequence corresponds to the 5' end of the respective mRNAs and includes 3–4 nucleotides present upstream of the initiation codon.

TABLE II. Antisense Oligos to p65 Inhibit Adhesion of Diverse Cell Lines

Diverse cell lines of murine and human origin, including fibroblasts, stromal, neuronal, endothelial, and epithelial cells, were exposed to 30 μM of p65 oligos (murine or human) and photographed after 48 to 72 hours. Marked effects on cell adhesion were observed with each of the cell lines listed.

TABLE I

| GENE | SPECIES | SEQUENCE (5' TO 3') | REFERENCE |
|---|---|---|---|
| P65-S | MURINE | ACC ATG GAC GAT CTG TTT CCC CTC [SEQ ID:11] | 6 |
| P65-AS | MURINE | GAG GGG AAA CAG ATC GTC CAT GGT [SEQ ID:12] | 6 |
| P65-S | HUMAN | GCC ATG GAC GAA CTG TTC CCC [SEQ ID:1] | 7 |
| P65-AS | HUMAN | GGG GAA CAG TTC GTC CAT GGC [SEQ ID:3] | 7 |
| P50-S | MURINE | ACC ATG GCA GAC GAT CCC [SEQ ID:13] | 4 |
| P50-AS | MURINE | GGG ATC GTC TGC CAT GGT [SEQ ID:14] | 4 |
| P50-S | HUMAN | AGA ATG GCA GAA GAT CCA [SEQ ID:2] | 5 |
| P50-AS | HUMAN | TGG ATC TTC TGC CAT TCT [SEQ ID:4] | 5 |

TABLE II

| CELL LINE | CELL TYPE | ANTI-SENSE OLI-GOS[1,2,3] |
|---|---|---|
| Murine | | |
| 3T3 FEEDER CELLS (PRIMARY) | FIBROBLAST | m p65 |
| RAT-1 | FIBROBLAST | m p65 |
| NIH 3T3 | FIBROBLAST | m p65 |
| S-17 | BONE MARROW STROMAL CELLS | m p65 |
| PC-12 | PHEOCHROMOCYTOMA | m p65 |
| Human | | |
| PRIMARY HUVECS | ENDOTHELIAL | h p65 |
| RHEK-1 | EPITHELIAL | h p65 |
| PRIMARY KERATINOCYTES | EPITHELIAL | h p65 |

[1] The inhibitory effects of antisense oligos on cell adhesion were species specific.
[2] The corresponding sense oligonucleotide had no effect.
[3] The p50 sense or oligos did not inhibit adhesion of these cells.

We claim:
1. An oligodeoxynucleotide having the nucleotide sequence set forth as SEQ ID NO: 3.
2. An oligodeoxynucleotide of claim 1 wherein the nucleotides are connected by a phosphate group having the formula:
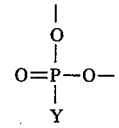
wherein Y is selected from the group consisting of methyl, oxygen and sulfur.
* * * * *

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA ( i i i ) HYPOTHETICAL: NO ( i v ) ANTI-SENSE: NO ( x i ) SEQUENCE DESCRIPTION: SEQ ID NO:1:

GCCATGGACG AACTGTTCCC C      21

( 2 ) INFORMATION FOR SEQ ID NO:2:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( i i ) MOLECULE TYPE: DNA ( i i i ) HYPOTHETICAL: NO ( i v ) ANTI-SENSE: NO ( x i ) SEQUENCE DESCRIPTION: SEQ ID NO:2:

AGAATGGCAG AAGATCCA    18

( 2 ) INFORMATION FOR SEQ ID NO:3:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: DNA ( i i i ) HYPOTHETICAL: NO ( i v ) ANTI-SENSE: YES ( x i ) SEQUENCE DESCRIPTION: SEQ ID NO:3:

GGGGAACAGT TCGTCCATGG C    21

( 2 ) INFORMATION FOR SEQ ID NO:4:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( i i ) MOLECULE TYPE: DNA ( i i i ) HYPOTHETICAL: NO ( i v ) ANTI-SENSE: YES ( x i ) SEQUENCE DESCRIPTION: SEQ ID NO:4:

TGGATCTTCT GCCATTCT    18

( 2 ) INFORMATION FOR SEQ ID NO:5:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( i i ) MOLECULE TYPE: DNA ( i i i ) HYPOTHETICAL: NO ( i v ) ANTI-SENSE: NO ( x i ) SEQUENCE DESCRIPTION: SEQ ID NO:5:

GCGGCCAAGC TTAAGATCTG CCGAGTAAAC    30

( 2 ) INFORMATION FOR SEQ ID NO:6:

( i ) SEQUENCE CHARACTERISTICS:
  ( A ) LENGTH: 33 base pairs
  ( B ) TYPE: nucleic acid
  ( C ) STRANDEDNESS: single

- continued (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:6:

GCGTGCTCTA GAGAACACAA TGGCCACTTG CCG 33

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:7:

AAAGGTTATC GTTCAGTT 18

(2) INFORMATION FOR SEQ ID NO:8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:8:

TTGTAGATAG GCAAGGTC 18

(2) INFORMATION FOR SEQ ID NO:9:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:9:

ACCGCTCGAG CTAAGCCCGGG ACCCTGACCA TGGAC 35

(2) INFORMATION FOR SEQ ID NO:10:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (  i i i  ) HYPOTHETICAL: NO (  i v  ) ANTI-SENSE: NO (  x i  ) SEQUENCE DESCRIPTION: SEQ ID NO:10:

CCGGAATTCG CTAGCGCTTC ACACACTGGA TCCCCAGG 38

( 2 ) INFORMATION FOR SEQ ID NO:11:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( x i ) SEQUENCE DESCRIPTION: SEQ ID NO:11:

ACCATGGACG ATCTGTTTCC CCTC 24

( 2 ) INFORMATION FOR SEQ ID NO:12:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: YES ( x i ) SEQUENCE DESCRIPTION: SEQ ID NO:12:

GAGGGGAAAC AGATCGTCCAA TGGT 24

( 2 ) INFORMATION FOR SEQ ID NO:13:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( x i ) SEQUENCE DESCRIPTION: SEQ ID NO:13:

ACCATGGCAG ACGATCCC 18

( 2 ) INFORMATION FOR SEQ ID NO:14:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: YES ( x i ) SEQUENCE DESCRIPTION: SEQ ID NO:14:
GGGATCGTCT GCCATGGT 18